US011023705B2

(12) United States Patent
Woerdemann et al.

(10) Patent No.: US 11,023,705 B2
(45) Date of Patent: Jun. 1, 2021

(54) METHOD FOR THE CYTOMETRIC ANALYSIS OF CELL SAMPLES

(71) Applicant: OLYMPUS SOFT IMAGING SOLUTIONS GMBH, Muenster (DE)

(72) Inventors: Mike Woerdemann, Ostbevern (DE); Stefan Diepenbrock, Muenster (DE); Sascha Hoefling, Nottuln (DE); Daniel Krueger, Berlin (DE)

(73) Assignee: OLYMPUS SOFT IMAGING SOLUTIONS GMBH, Münster (DE)

( * ) Notice: Subject to any disclaimer, the term of this patent is extended or adjusted under 35 U.S.C. 154(b) by 113 days.

(21) Appl. No.: 15/945,288

(22) Filed: Apr. 4, 2018

(65) Prior Publication Data

US 2018/0293426 A1    Oct. 11, 2018

(30) Foreign Application Priority Data

Apr. 5, 2017  (DE) .......................... 102017107348.5

(51) Int. Cl.
*G06K 9/00* (2006.01)
*G01N 15/14* (2006.01)
(Continued)

(52) U.S. Cl.
CPC ....... *G06K 9/00127* (2013.01); *G01N 15/147* (2013.01); *G01N 15/1434* (2013.01);
(Continued)

(58) Field of Classification Search
None
See application file for complete search history.

(56) References Cited

U.S. PATENT DOCUMENTS 4,661,913 A    4/1987  Wu et al.
5,247,339 A    9/1993  Ogino
(Continued)

FOREIGN PATENT DOCUMENTS

CN    2530263 Y    1/2003
CN    103154732 A    6/2013
(Continued)

OTHER PUBLICATIONS

Japanese Notice of Reasons for Refusal dated Feb. 12, 2020 received in Japanese Patent Application No. 2018-073062, together with an English-language translation.
(Continued)

*Primary Examiner* — Bernard Krasnic
(74) *Attorney, Agent, or Firm* — Scully, Scott, Murphy & Presser, P.C.

(57) ABSTRACT

The present application relates to a method for the cytometric analysis of multiple cell samples by a microscope for examining multiple cell samples under a microscope, wherein the microscope can be or is operated, selectively and/or alternatingly, in a transmission mode and/or in a fluorescence mode, and wherein at least one cell sample has at least one fluorescence marker. The method includes; moving the cell samples continuously in one plane relative to an optical system of the microscope having at least one microscope camera, wherein, during the movement of the cell samples, at least one or more images of a sub-region of the cell samples are recorded in the transmission mode or in the fluorescence mode and at least one or more images of the same sub-region of the cell samples are recorded in the fluorescence mode by the at least one microscope camera.

19 Claims, 6 Drawing Sheets

(51) Int. Cl.
*G16H 30/20* (2018.01)
*G01N 21/64* (2006.01)
*G01N 21/85* (2006.01)
*G16H 10/40* (2018.01)
*G16H 40/63* (2018.01)
*G01N 15/10* (2006.01)
*G01N 15/02* (2006.01)
*G01N 15/06* (2006.01)

(52) U.S. Cl.
CPC ..... *G01N 15/1459* (2013.01); *G01N 15/1463* (2013.01); *G01N 15/1475* (2013.01); *G01N 21/6428* (2013.01); *G01N 21/6458* (2013.01); *G01N 21/85* (2013.01); *G16H 10/40* (2018.01); *G16H 30/20* (2018.01); *G16H 40/63* (2018.01); *G01N 2015/0294* (2013.01); *G01N 2015/0693* (2013.01); *G01N 2015/1006* (2013.01); *G01N 2015/1445* (2013.01); *G01N 2015/1452* (2013.01); *G01N 2015/1472* (2013.01); *G01N 2015/1486* (2013.01); *G01N 2015/1493* (2013.01); *G01N 2015/1497* (2013.01); *G01N 2021/6491* (2013.01)

(56) References Cited

U.S. PATENT DOCUMENTS

| | | | |
|---|---|---|---|
| 5,856,665 A | 1/1999 | Price et al. | |
| 6,169,816 B1 | 1/2001 | Ravkin | |
| 6,211,955 B1 | 4/2001 | Basiji et al. | |
| 6,259,807 B1* | 7/2001 | Ravkin | G01N 15/1475 382/133 |
| 6,615,141 B1* | 9/2003 | Sabry | G06K 9/00127 702/19 |
| 2002/0146734 A1* | 10/2002 | Ortyn | C12Q 1/6841 435/6.11 |
| 2006/0068371 A1* | 3/2006 | Ortyn | G01J 3/2889 435/4 |
| 2009/0212242 A1 | 8/2009 | Yamada | |
| 2010/0135566 A1 | 6/2010 | Joanidopoulos et al. | |
| 2010/0232675 A1* | 9/2010 | Ortyn | G01N 15/147 382/134 |
| 2010/0246927 A1 | 9/2010 | Arbuckle | |
| 2014/0030729 A1* | 1/2014 | Basiji | G01N 33/57492 435/6.14 |
| 2014/0231638 A1 | 8/2014 | Damaskinos et al. | |
| 2014/0334696 A1* | 11/2014 | Gholap | G06T 3/4038 382/128 |
| 2015/0080233 A1* | 3/2015 | Bendall | H01J 49/0004 506/4 |
| 2016/0250298 A1* | 9/2016 | Ruiz-Avila | A61Q 19/00 424/401 |
| 2016/0282325 A1* | 9/2016 | Nolan | G01N 33/5008 |
| 2016/0327469 A1 | 11/2016 | Sharpe et al. | |
| 2016/0335478 A1* | 11/2016 | Bredno | G06K 9/00147 |
| 2016/0371834 A1* | 12/2016 | Watanabe | G06K 9/00147 |
| 2017/0037483 A1* | 2/2017 | Hayashi | C12N 5/0657 |
| 2018/0153819 A1* | 6/2018 | Koike | A61K 9/5169 |
| 2018/0372640 A1* | 12/2018 | Kaneko | G01N 21/6428 |

FOREIGN PATENT DOCUMENTS

| | | |
|---|---|---|
| CN | 105445170 A | 3/2016 |
| DE | 19754909 A1 | 6/1999 |
| DE | 69926116 T2 | 4/2006 |
| DE | 69832167 T2 | 7/2006 |
| DE | 102008059788 A1 | 8/2010 |
| DE | 102011075369 A1 | 11/2012 |
| JP | 3113909 B2 | 12/2000 |
| JP | 2002-514304 A | 5/2002 |
| JP | 2006-38977 A | 2/2006 |
| JP | 2009-14939 A | 1/2009 |
| JP | 2013-3338 A | 1/2013 |
| JP | 2015-90471 A | 5/2015 |
| WO | WO 99/30278 A1 | 6/1999 |
| WO | WO 99/44488 A2 | 9/1999 |
| WO | WO 2008/005426 A2 | 1/2008 |
| WO | 2010/004691 A1 | 1/2010 |
| WO | WO-2015162810 A1 * | 10/2015 |

OTHER PUBLICATIONS

Chinese Office Action dated Apr. 9, 2020 received in Chinese Application No. 201810299191.4, together with an English-language translation.

* cited by examiner

Incremental movement of the cell samples

Illumination time 1 ms

Continuous movement of the cell samples

Illumination time 50 μs

METHOD FOR THE CYTOMETRIC ANALYSIS OF CELL SAMPLES

CROSS-REFERENCE TO RELATED APPLICATION

The present application is based upon and claims the benefit to DE 10 2017 107 348.5 filed on Apr. 5, 2017, the entire contents of each of which are incorporated herein by reference.

BACKGROUND

Field

The present application relates to a method for the cytometric analysis of multiple cell samples.

Prior Art

Cytometric analysis methods for the image-based analysis of fluorescence stained cells, for example, are known in the field of cytometry, wherein, in addition to the parameters or respectively features of image-based cytometry that are known from classic cytometry, the number of available parameters or respectively features has multiplied, since the object size (especially the cell size) and other morphological parameters of respective images of the cell samples recorded microscopically, possibly by fluorescence microscopy, are obtained alongside the parameters known from classic cytometry (typically color (or respectively wavelength), intensity and scattered light signal).

Further methods are known, by means of which the fluorescence properties of samples, such as tissue samples or cell cultures, are examined using imaging and non-imaging methods. Various methods also permit the fluorescence intensities of individual biological cells and cell components to be determined. The fluorescence intensity is quantified, for example, in a flow cytometer or in an imaging flow cytometer by means of an imaging time delay integration detector (TDI detector), or by means of pulsed illumination, or by scanning the sample with a laser beam.

Moreover, flow cytometry is known as a method for the quantitative fluorescence analysis of cells. In flow cytometry, a (dyed) cell suspension passes a focused laser beam, wherein the scattered and fluorescent light that is generated in this way is detected. During the measurement, the individual fluorescence-marked cells are conveyed through a capillary tube, where the individual cells flow through a flow cell, in which they are excited by laser light. The fluorescent dyes in the cells are excited by the laser beam, as a result of which the cells scatter laser light. In so doing, the light scattering and the emitted fluorescent light are detected.

Other methods for quantitative fluorescence analysis utilize conventional epifluorescence microscopes in combination with digital imaging and subsequent image analysis for fluorescence quantification. Samples and sample carriers are used in these methods so that adherent cells, for instance, can be directly analyzed in culture vessels, such as microtiter plates ("well plates").

There are also known methods for the high-speed recording of individual images of laterally adjacent regions of an object as well as a microscope for recording individual images of an object during successive image recording cycles and the subsequent composition of the individual images into a complete picture of the object.

For the purposes of scientific studies and quality control as well as for toxicology or diagnostics, respectively, it is known that the cells are added to a liquid cell-fixing solution or to a liquid buffer to quantify fluorescence samples in cell cultures, wherein the cells are typically covered with the liquid during the examination process.

In microscopic examinations, the cell samples are arranged in microscopy plates (microtiter plates; well plates) as sample carriers on a table, wherein the table is incrementally conveyed together with the sample carrier from one position to the next, and is stopped for the recording of an image. The sample carrier is then moved further. Because of the jerky movement of the sample carrier, the cells to be studied are subjected to acceleration forces and vibrations, which can bring about changes in the cell cultures and which also generates surface waves, and so the recording of transmission images is impeded.

Alternatively, to prevent oscillations on the samples to be studied, the entire optical system of a microscope or parts of the optics are moved relative to the sample carrier, whereby the heavy weight of the components of the microscope in question make it difficult to make quick movements.

An object of the present application consists in improving the fluorescence quantifications of cell samples, wherein the loads, especially mechanical loads, and exposure to light of the cell samples, such as in adherent cells, could be reduced, making the analysis relatively quick.

This object is solved by a method for the cytometric analysis of multiple cell samples by means of a microscope for microscoping multiple cell samples, wherein the microscope can be or is operated, selectively and/or alternatingly, in a transmission mode and/or in a fluorescence mode, or also in epifluorescence mode, and wherein at least one cell sample has at least one fluorescence marker, with the following method steps:

the cell samples are moved continuously in one plane relative to an optical system of the microscope having at least one microscope camera, wherein, during the movement of the cell samples, at least one or more images of a sub-region of the cell samples are recorded in the transmission mode or in the fluorescence mode and at least one or more images of the same sub-region of the cell samples are recorded, possibly in sections, in the fluorescence mode, or also in epifluorescence mode, by means of the at least one microscope camera, and the images can be digitized, wherein the at least one or more images of the same sub-region of the cell samples in the transmission mode or in the fluorescence mode, and at least one or more images of the same sub-region of the cell samples in the fluorescence mode are associated with each other, possibly locally, and a.) wherein the positions and/or contours of cells or cell components of the cell samples are detected in the images of the transmission mode, and the detected intensities of the images recorded in the fluorescence mode are then analyzed as a function of the detected positions and/or contours of cells or cell components in the cell samples, and/or b.) wherein the positions and/or contours of cells or cell components of the cell samples are detected in the images of the fluorescence mode, and the detected intensities of the images recorded in the transmission mode are then analyzed as a function of the detected positions and/or contours of cells or cell components in the cell samples, and/or c.) wherein the positions and/or contours of cells or cell components of the cell samples are detected in the images of the fluorescence mode, and the detected intensities of the images recorded in a further fluorescence mode are then analyzed as a function of the detected positions and/or contours of cells or cell components in the cell samples.

The present application is based on the idea that one or more cell samples with fluorescence marker molecules are moved relative to an optical system of a microscope, wherein pictures, or respectively images, of sub-regions of the cell samples are alternatingly recorded i.) alternating between the transmission mode and the fluorescence mode or ii.) only in the fluorescence mode. During alternating operation of the microscope, which permits images that are (sufficiently) illuminated for digital image analysis despite short illumination times, the arrangement of the cells, the cell structures and/or subcellular regions are detected, and the fluorescence of the examined sub-regions are then recorded so that a fluorescence quantification can subsequently be carried out.

Within the scope of the present application, it is possible that the microscope is operated, possibly exclusively, in the fluorescence mode, wherein, during the movement of the cell samples, at least one or more images of a sub-region of the cell samples are recorded in a first fluorescence mode and at least one or more images of the same sub-region of the cell samples are then recorded, possibly in sections, in a second fluorescence mode by means of the at least one microscope camera, and subsequently the at least one or more images of the same sub-region of the cell samples in the first fluorescence mode and at least one or more images of the same sub-region of the cell samples in the second fluorescence mode are associated with each other, possibly locally. Subsequently, the positions and/or contours of cells or cell components of the cell samples are detected in the images of the first fluorescence mode, and the detected intensities of the images recorded in the second fluorescence mode are then analyzed as a function of the detected positions and/or contours of cells or cell components in the cell samples in the first fluorescence mode.

Owing to the continuous movement of the cell samples and the brief illumination times, which are made possible by the detection of the cells and cell components in the cell samples in the bright transmission channel, it is possible to reduce the effects on the cells such as phototoxicity as well as other damage caused by light, wherein mechanical vibrations or acceleration forces that affect cell viability are also reduced at the same time. A method is hereby provided, and it is also less invasive to the quantification of cell information about individual or multiple adherent cells. Since this method protective of cells and, at the same time, in contrast to a flow cytometric analysis, can also be repeated on the same sample at a later stage, it is also suited for temporal live cell analysis, in which the method is repeated at multiple successive points in time.

Using the optical microscopy system with at least one digital camera, more information can be obtained from sub-cellular regions within individual cells. In this instance, the optical microscopy system is arranged together with the digital camera or cameras in such a way that images are recorded from a limited field of view of all cell samples or from one sample region. The images recorded of the sub-region are digitally recorded by the at least one microscopy camera, wherein the images are digitalized and are stored according to the imaging method, i.e. in the transmission mode or in the fluorescence mode, or are analyzed directly while the samples to be studied are continuously moved relative to the optical system of the microscope.

Depending upon the imaging method, i.e. the transmission mode or the fluorescence mode, images are recorded from mutually overlapping fields of view. The images of the examined sub-region recorded in the transmission mode or in the (first) fluorescence mode are then associated with corresponding images recorded in the fluorescence mode or in the second fluorescence mode from the corresponding sub-region, and so regions of cell samples that are of interest can subsequently be further studied.

While the cell samples are moving, at least one or more images of a sub-region of the cell samples are recorded in the transmission mode or in the fluorescence mode, and then at least one or more images of the same sub-region are recorded, wherein, because the cell samples are moving compared to the previously recorded first images, one or more sections of the same sub-region are recorded in the second, later images.

According to the present application, a method for automatically analyzing biological cells or cell samples is provided, wherein a large number of individual cells or cell components can be examined using methods from the fields of microscopy and digital image analysis in order to conduct a quantitative analysis of the fluorescence intensity.

Additionally, it is further advantageous in one embodiment of the method that at least one image of the sub-region of the cell samples in the transmission mode that is offset in time, later or earlier, is modified with respect to a predetermined first image of the sub-region of the cell samples in the transmission mode as a function of the temporal offset or as a function of the relative displacement of the cell samples with respect to the at least one microscopy camera between the predetermined first image and the temporally offset image, so that the first predetermined image and the temporally offset image are associated with the same sub-region of the cell samples.

Because two temporally offset images are recorded of the detected sub-region of the cell samples, the two images in the transmission mode are correctly superimposed over each other by virtual position correction as a function of the displacement of the cell samples during the period between when the images were recorded.

Additionally, an embodiment of the method is distinguished by the fact that at least one temporally offset, later or earlier, image of the sub-region of the cell samples in the fluorescence mode with respect to a predetermined first image of the sub-region of the cell samples in the fluorescence mode is modified as a function of the temporal offset or as a function of the relative displacement of the cell samples with respect to the at least one microscopy camera between the predetermined first image and the temporally offset image, so that the first predetermined image and the temporally offset image are associated with the same sub-region of the cell samples.

As with the images of the same sub-region that were recorded in the transmission mode, for the images of the same sub-region recorded in the fluorescence mode, the images of the sub-region recorded at different times are also superimposed over each other after they are recorded in a way that accounts for the displacement path of the cell samples between the images recorded at different times, since the cell samples are moved continuously, and in some embodiments linearly, between the two images.

Furthermore, it is considered advantageous in one embodiment of the method that the movement of the cell samples will be synchronized with the chronological sequence of the images of the sub-region of the cell samples.

As a function of the continuous, in some embodiments uniform, movement of the cell samples with respect to the optical system of the microscope, which in some embodiments is stationary, by means of which the images are recorded in the transmission mode and in the fluorescence mode, images or respectively pictures of the sub-regions of the cell samples are continuously recorded and saved at predetermined regular intervals and are then analyzed and evaluated in a subsequent method step.

According to the present application, an apparatus for moving the cell samples is provided or present, wherein said apparatus has a control apparatus, by means of which trigger signals, in some embodiments electronic trigger signals, are generated at predetermined positions on the cell samples so that the camera taking the images and at least one light source for the different image types, i.e. images in the transmission mode or in the fluorescence mode, are synchronized.

Moreover, it is provided in an advantageous embodiment of the method that at least one image of the sub-region of the cell samples in the transmission mode is recorded in a first plane, in some embodiments a focused first plane, and at least one image of the sub-region of the cell samples in the transmission mode is recorded in a second plane, in some embodiments a defocused plane, which is different from the first plane.

Furthermore, at least two images of the sub-region, or respectively the same sub-region, of the cell samples are advantageously recorded in the fluorescence mode, and in some embodiments recorded in the epifluorescence mode.

In addition, the method in one embodiment is distinguished by the fact that after the images of the sub-region of the cell samples have been recorded in the transmission mode and in the fluorescence mode, further images are recorded in the transmission mode and/or in the fluorescence mode for a sub-region of the cell samples that is adjacent, in some embodiments immediately adjacent, to the preceding sub-region of the cell samples, wherein the further images are recorded in the same way for the adjacent sub-region as for the preceding, and in some embodiments the first sub-region, sub-region of the cell samples.

By recording multiple images of multiple adjacent sub-regions of the cell samples, it is possible that a larger region of the cell samples can be examined, which permits an automated cytometric analysis of cell samples in greater numbers.

Furthermore, it is advantageous in one embodiment of the method that the images of the cell samples in the transmission mode for multiple sub-regions of the cell samples are all combined into one complete image in the transmission mode and/or that the images of the cell samples in the fluorescence mode for multiple sub-regions of the cell samples are all combined into one complete image in the fluorescence mode.

In other embodiments, during the implementation of the method that the images of each image type, in the transmission mode or in the fluorescence mode, or the complete images of each image type, including in the transmission mode or in the fluorescence mode, be analyzed in some embodiments by automated means. For this purpose, images or respectively pictures from a suitable recording mode, such as by a transmission mode, are examined for the presence of, for instance, individual cells or cell components using methods from digital image processing and analysis, and the position and/or contours of the detected objects, i.e. the positions and/or contours of cells or cell components of the cell samples, are identified or determined, whereby it is possible to quantify the fluorescence intensities of the same objects in the pictures taken in the other imaging mode once the virtual position correction has been performed. The object masks for the objects or respectively segmentation masks can directly be identified and determined in the transmission mode because, when determining the segmentation masks in a picture that was taken in a fluorescence mode, the measurement can be subject to an error due to the lack of independence. Determining the segmentation masks or respectively the object masks in a picture taken in fluorescence mode is well-suited for situations in which substantially longer illumination times are used and therefore a higher signal-to-noise ratio or respectively higher contrast is achieved.

Furthermore, in one embodiment of the method it is practical for phase-contrast images to be generated from the images in the transmission mode or from the complete images in the transmission mode. It is further disclosed in one embodiment of the method that the images obtained in the transmission mode are already recorded as phase-contrast images.

Regions of the cell samples that are of interest can be determined from phase-contrast transmission images, whereby the contrast of images is increased in transparent or semi-transparent cell samples, such as un-dyed cells. For example, phase-contrast images are generated that are created by the Zernicke phase-contrast method or by the differential interference contrast (DIC) method.

Additionally, phase-contrast images can also be obtained by the use of defocused transmission images, wherein the phase contrast by aberrations due to defocusing is used, wherein it is possible that the contrast is maximized later by digital image processing of the images.

Phase-contrast images can also be obtained by quantitative phase measurements or estimation methods, such as digital holography methods or ptychography-based methods.

It is further disclosed that phase-contrast images can also be obtained which are based on Transport of Intensity Equation (TIE) methods.

Furthermore, it is possible in one configuration that defocused images can be achieved by utilizing the properties of the longitudinal chromatic aberration of the optical system or respectively imaging system. In this embodiment, it is provided in one configuration that the sample is subsequently illuminated with light having different wavelengths. Alternatively, images are recorded by means of an RGB camera or using chromatic filters in the optical path between the cell samples and the at least one camera.

It is also provided in the method that RGB transmission images of the sub-regions are also obtained in the transmission mode.

By means of the phase-contrast images obtained or created, it is possible to use the images to determine the positions and/or contours of cells or cell components in the individual cell samples. The position and/or contour information about the cells and/or cell components make it possible to measure intensity in the locally associated fluorescence image(s), and these measurements are associated with the identified cells and/or cell components of the cell samples. Also, various cell types or cell properties can be appropriately classified using the intensity measurements.

To carry out the method, a microscopy apparatus, in some embodiments, having an automated wide-field microscope with a camera, is provided for examining and imaging live cells, for example. In this instance, the apparatus is operated in the bright field method or a phase-contrast method for the transmission mode and in the reflection method for the fluorescence mode.

The method is thus operated in a "cytometry mode," wherein the cells and the cellular structures are detected and the corresponding fluorescence intensities are determined by means of the method described above, in a relatively fast, continuous imaging mode. Data or respectively image data about the cell samples, for example, that are usually obtained by a flow cytometry-based analysis are obtained in this mode. In contrast to flow cytometry, in which one works with non-adherent cells suspended in liquids, the method according to the present application also permits work with adherent cells in microtiter plates, or respectively well plates in the cytometry mode.

In a subsequent screening mode, high-quality images of multiple sub-regions of the cell samples can automatically be recorded in the transmission mode and in the fluorescence mode.

During the implementation of the method, the samples, or respectively cell samples, are moved in an X-Y plane in front of a stationary objective so that the entire region is continuously imaged by a camera of the microscope. The cell samples are moved continuously, and in some embodiments linearly, in the X-Y plane. The images of the sub-regions of the cell samples obtained in this way are then optionally merged into a larger, seamless image, wherein the partial pictures or respectively partial images are accordingly merged.

During the continuous movement of the cell samples relative to the microscope objective, the images of the sub-regions of the cell samples can be obtained continuously and at regular intervals. It is understood here that the image position is adjusted by autofocus during the continuous movement in the transmission mode. For example, the image position is set in the focus of an upper substrate plane or according to a different method.

While images of the cell samples are being taken, the position data of the cell samples, or respectively cell sample carriers corresponding to each obtained image are recorded.

Thus it is provided for the implementation of the method that the transmitted light is detected in the transmission mode in at least two Z planes simultaneously or in quick succession.

Usually, images are likewise recorded in one or more fluorescence channels. The recorded images of the sub-region in the fluorescence mode can be of lower quality and are not necessarily used for visualization. Instead, the images in the fluorescence mode are recorded for intensity measurements over a predetermined region.

Because short light pulses are used during or respectively for the recording of images, the cell samples are exposed to the light for a short time, and so blurry images during the continuous movement of the sample carrier can be prevented. The illumination time of the samples is typically shorter than 100 µs or shorter than 50 µs. Light-emitting diodes (LEDs) can be used to illuminate the samples.

Apart from the significant reductions in recording times for the images of the cell samples, a further advantage of the method according to the present application consists in that the cell samples can be examined multiple times for further image recordings and analyses, since the cell samples are arranged on microtiter plates ("well plates") and the microtiter plates are moved for the further image recordings by means of the microscopy system.

Further features of the present application will become apparent from the description of inventive embodiments in conjunction with the claims and the attached drawings and diagrams. Embodiments according to the present application can be realized by individual features or by a combination of multiple features.

BRIEF DESCRIPTION OF THE DRAWINGS

Without restricting the general inventive concept, the present application will be described below on the basis of the embodiments with reference to the drawings and diagrams, wherein reference is made to the drawings and diagrams. The following is illustrated.

DETAILED DESCRIPTION

Figure 1:
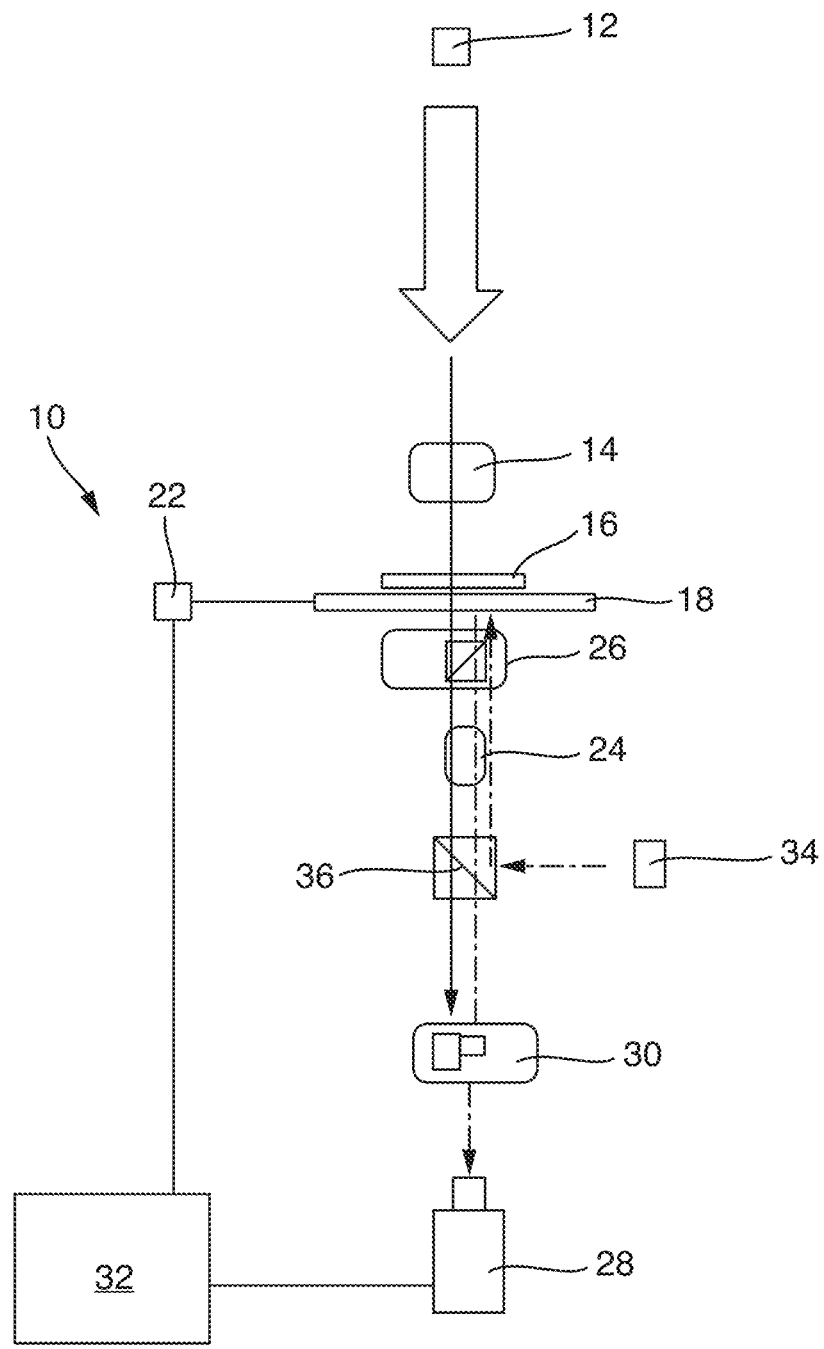
FIG. 1 illustrates a schematic representation of an arrangement for examining cell samples under a microscope.

A basic arrangement 10 for examining cell samples under a microscope, by means of which the method for the cytometric analysis of cell samples can be carried out, is schematically illustrated in FIG. 1.

The arrangement 10 has a light source 12, by means of which light is transmitted through a condenser lens 14 onto a sample carrier 16. The sample carrier 16 in this instance is arranged on a mobile table 18, which can be displaced in the X-Y plane by a motor 22. By means of the light source 12, which can be a light-emitting diode or light-emitting diodes, or any other suitable light source, the cell samples on the sample carrier 16 are transilluminated in the transmission mode, and so the light passing through the cell samples is then detected by an objective 24 and by a digital camera 28. In this way, images of sub-regions of the cell samples are digitally recorded by the digital camera 28.

After the light has passed through the cell samples between the table 18 and the objective 24, a device 26 can be provided in the beam path between the light source 12 and the digital camera 28 to provide focus in the Z plane. Furthermore, it is possible in one embodiment for a further optical element 30 to be provided between the objective 24 and the digital camera 28 in the beam path of the light in transmission mode in order to record images in two parallel Z planes of the cell samples.

The light source 12 can be configured as a light-emitting diode (LED), wherein the light source 12 generates flashes of light lasting e.g. less than 50 µs. It can also be provided that the light source 12 has a plurality of light-emitting diodes that produce light at different wavelengths. The light-emitting diodes can be activated simultaneously or successively.

The mobile table 18 is moved continuously at a speed of 20 mm/sec, for example, in the X-Y plane.

The images recorded by the digital camera 28 are transmitted to a computer 32 so that the digitized images can be saved and processed by a processor of the computer 32. The computer 32 is configured as a control device for the motor 22 and is linked with the motor 22 such that the table 18 is controlled synchronously and moved at a predetermined speed. As a result, the movements of the sample carrier 16 are synchronized with the images recorded by the digital camera 28 in a positionally accurate way.

Moreover, the computer 32 is also linked to the light source 12 (not illustrated), whereby the circuit of the light source 12 is likewise synchronized.

A light source 34 with which fluorescent light is generated is arranged below the table 18 in order to illuminate the cell samples in the subsequent fluorescence mode after the images of the cell samples of a sub-region have been recorded in the transmission mode. By means of the generated fluorescent light and, for example, after passing through an excitation filter, the generated light is deflected or respectively reflected by a beam splitter 36 toward the cell samples, i.e. in the direction of the table 18, so that the short-wave exciting light strikes the cell samples in the sample carrier 16. The cell samples are provided with a fluorescence marker or the like so that longer-wave fluorescent light is emitted after, or immediately after, the absorption of the excitation light, whereby the radiated fluorescent light strikes the beam splitter 36 and, owing to the semitransparency of the beam splitter 36, the longer-wave fluorescent light passes the beam splitter 36 without deflection and, possibly after passing through a blocking filter, is recorded by the digital camera 28.

The picture taken by the digital camera 28 is based on the fluorescent light radiated by the cell samples. Multiple images of the sub-region of the cell samples can be recorded in the fluorescence mode.

Figure 2:
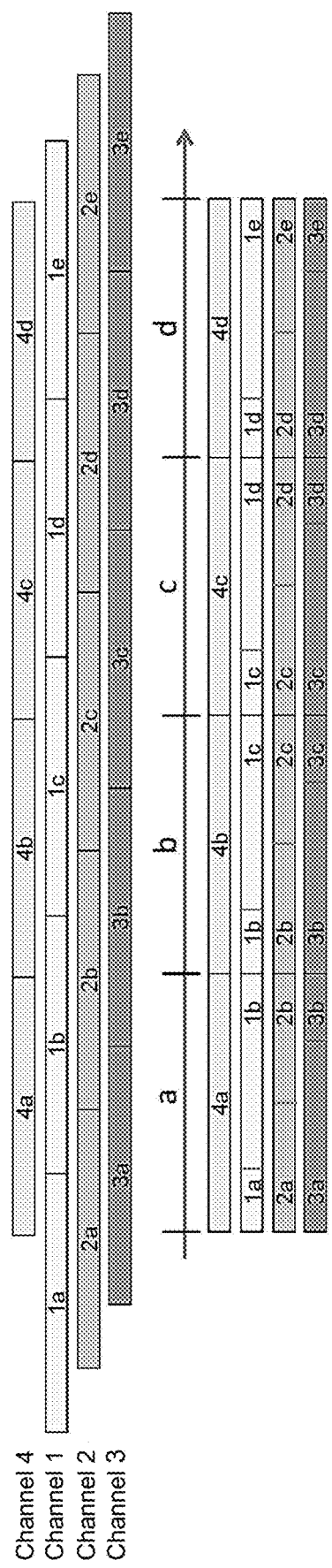
FIG. 2 illustrates a schematic representation of the recording process for carrying out the method for the cytometric analysis of cell samples.

The recording process for images of sub-regions of cell samples, for example by means of a microscope (cf. FIG. 1), is schematically illustrated in FIG. 2, wherein the microscope is operated alternatingly in the transmission mode and in the fluorescence mode. The images obtained in this way are then used for the cytometric analysis of the cell samples.

The respective position of a sample carrier with cell samples is indicated in the upper part of FIG. 2, wherein the cell samples are moved continuously from left to right relative to the microscope camera of the optical system of the microscope. During the continuous movement of the sample carrier, four images 1a, 2a, 3a, 4a of a first sub-region a of the cell samples are recorded successively in an image cycle. In the following image cycle, images 1b, 2b, 3b, 4b of sub-region b of the cell samples are recorded by the digital camera of the microscopy system. Similarly, after the second image cycle, images 1c, 2c, 3c, 4c are recorded in succession in the third image cycle. Thereafter, images 1d, 2d, 3d, 4d for sub-region d of the cell samples are recorded and saved in the fourth image cycle.

In each image cycle, four images of the respective sub-regions a, b, c and d, etc., are successively recorded in four image channels (1, 2, 3, 4), while the cell samples on the sample carrier are moved continuously, and optionally linearly, in a direction relative to the stationary microscopy system. The first image 1a, 1b, 1c, 1d of each sub-region a, b, c or d is a focused light field image in the transmitted light method as a first transmission image. The last image 4a, 4b, 4c, 4d of each sub-region a, b, c or d is a defocused light field image of the respective sub-region.

Subsequently, as the third (3a, 3b, 3c, 3d) and fourth (4a, 4b, 4c, 4d) images of an image cycle, two different images of sub-regions a, b, c or d, etc., are accordingly recorded as fluorescence images for various wavelengths. The four images 1a, 2a, 3a, 4a of the first image cycle for sub-region a of the cell samples are each recorded separately and saved separately, e.g. in separate storage channels. Then, in the second image cycle, both the transmission images 1b, 2b and the fluorescence images 3b, 4b are accordingly each saved in the appropriate storage channels for the four different images per image cycle.

After multiple sub-regions or the cell samples in their entirety have been detected, the respective associated images of the sub-regions in the respective imaging mode are associated with each other, in some embodiments associated locally.

Furthermore, for a cytometric evaluation of the cell samples, the temporally offset images of a sub-region are modified as a function of the temporal offset, taking into account the displacement movement of the cell samples, and so the four images of an image cycle for the respective sub-region are associated with each other locally. Using this digital or respectively virtual image displacement, images 1a, 2a, 3a, 4a, for example, are locally associated with each other for sub-region a, as is shown in the lower region of FIG. 2. Since each of images 1a, 2a, 3a does not completely cover sub-region a, images 1b, 2b 3b from adjacent sub-regions that overlap with the sub-region in question are likewise proportionally associated with sub-region a. Sub-region a is thus completely imaged as a result. This also similarly occurs for images 1b, 2b, 3b, 4b together with images 1c, 2c, 3c as well as for the further images in the image cycles for sub-regions b, c and d.

As a result of the post-processing and the digital image displacement, with consideration of the displacement path and the displacement time of the sample carrier with the cell samples, the images are correctly associated with each other locally. For the overlap of images in the seam region between the respective images of the corresponding imaging mode, it is possible during post-processing that the images can be adapted to each other using conventional methods and can be combined into one large image or a corresponding complete image in the respective imaging mode.

Figure 3:
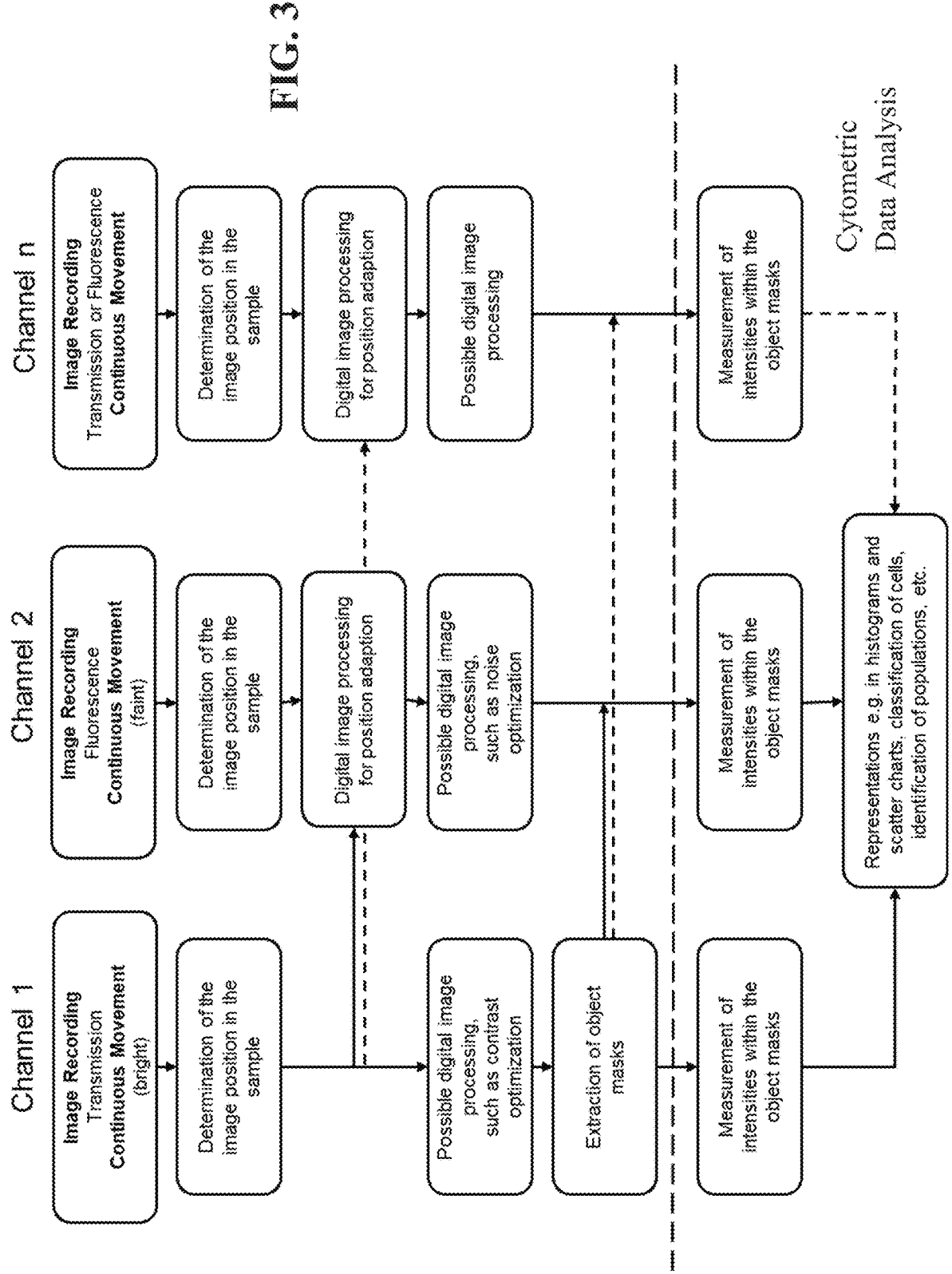
FIG. 3 illustrates a schematic representation of the method steps for the automatic microscoping and analysis of cell samples.

The method steps for the automatic microscoping and analysis of cell samples, including adherent cells, are illustrated schematically in FIG. 3.

In this case, images of sub-regions of cell samples are recorded in different channels, wherein sub-regions are alternately recorded in the transmission mode and in the fluorescence mode. In the process illustrated in FIG. 3, an image is first recorded in the transmission mode of the microscopy system in channel 1, wherein the sample carrier continues to be moved. Based on the position data of the sample carrier with the cell samples, the image position in the sample carrier or respectively in the sample is then determined. Here, the movement of the sample carrier with the cell samples is controlled by a control unit, whereby the image position can be determined on the basis of the control data from the control unit. Digital image processing, such as contrast optimization, is subsequently performed for the imaging of the sub-region in the bright transmission mode. Suitable object masks then, in some embodiments automatically, detect the contours of cells or subcellular structures in image channel 1 using appropriate recognition algorithms, etc.

Once the first sub-region of the cell samples has been imaged, a fluorescence image of the sub-region is recorded in a downstream image channel 2, wherein the image position of the image of the sub-region is then determined on the basis of the control data from the control unit for the sample carrier, whereby the position of the image recording is subsequently adapted by means of digital image displacement in a way that accounts for the displacement path and the displacement time with respect to the image recording in the first channel. Optionally, digital image processing, such as noise optimization of the identified signals, can then be carried out. Thereafter, as for image channel 1 and for image channel 2, corresponding image recordings are alternatingly recorded in the fluorescence mode or in the transmission mode of the cell samples while the cell samples continuously move, wherein the obtained image data are digitally displaced relative to a previous image in a post-processing step.

Corresponding digital image processing of the image recording takes place in the corresponding channel, if necessary. After the identified or predetermined object masks within the partial images are transmitted into the respective channels, the intensity measurements that have been obtained are then analyzed by a high-content screening analysis tool or cytometric analysis program. Here it is possible using cytometric data analysis to measure the intensities of the detected light in the transmission mode or in the fluorescence mode within the predetermined object masks. High-content screening (HCS) is a method or respectively a process for automatically recording and analyzing images of cells or cell samples, wherein the recorded images are evaluated, presented and analyzed here by means of image processing or respectively an image processing program. In this way, it is possible to analyze the cell samples cytometrically. Accordingly, this analysis makes it possible, for instance, to classify the cells. The classification obtained in this way can also serve as a quick pre-classification of a sub-group of cells, the activation of which is incrementally activated automatically later on in the procedure so that they can be recorded and analyzed with higher microscopic resolution, for example. The (data) analyses may be presented in histograms and scatter charts as well as by the classification of cells and the identification of populations, etc.

Figure 4A:
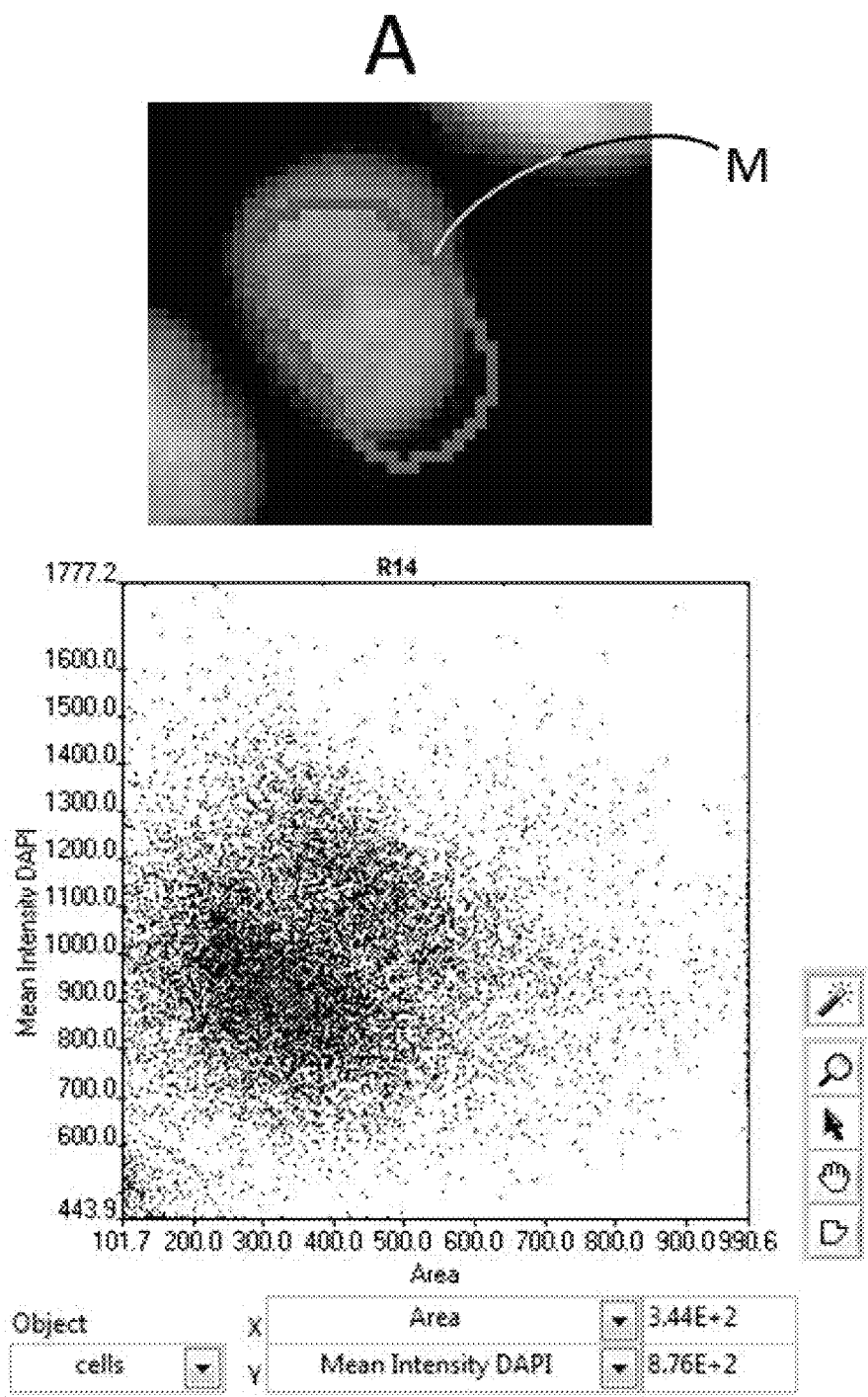
FIGS. 4A-4C illustrate image data of an individual fluorescence-stained cell nucleus and an associated cytometric evaluation of numerous cell nuclei.
Figure 4B:
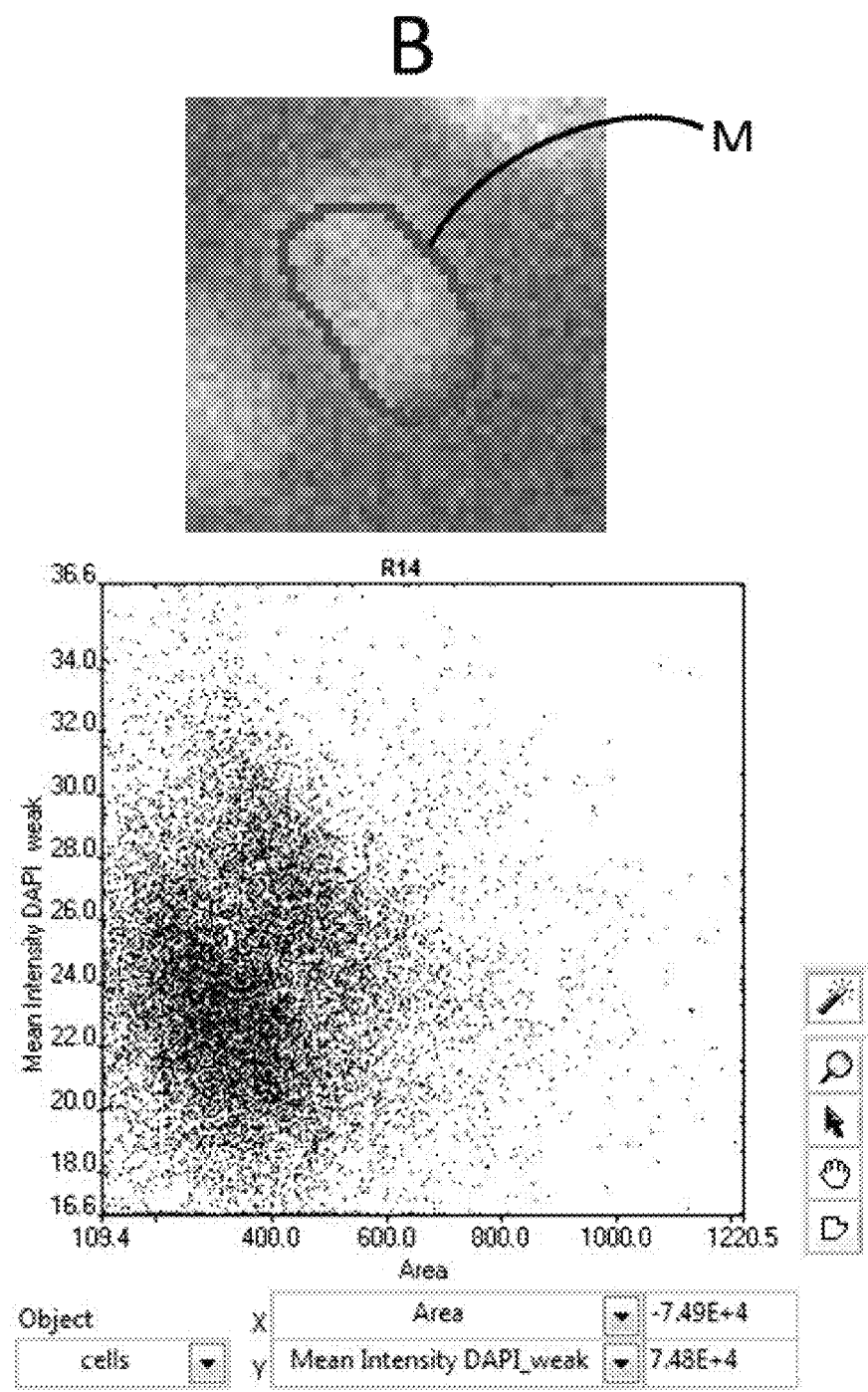
Figure 4C:
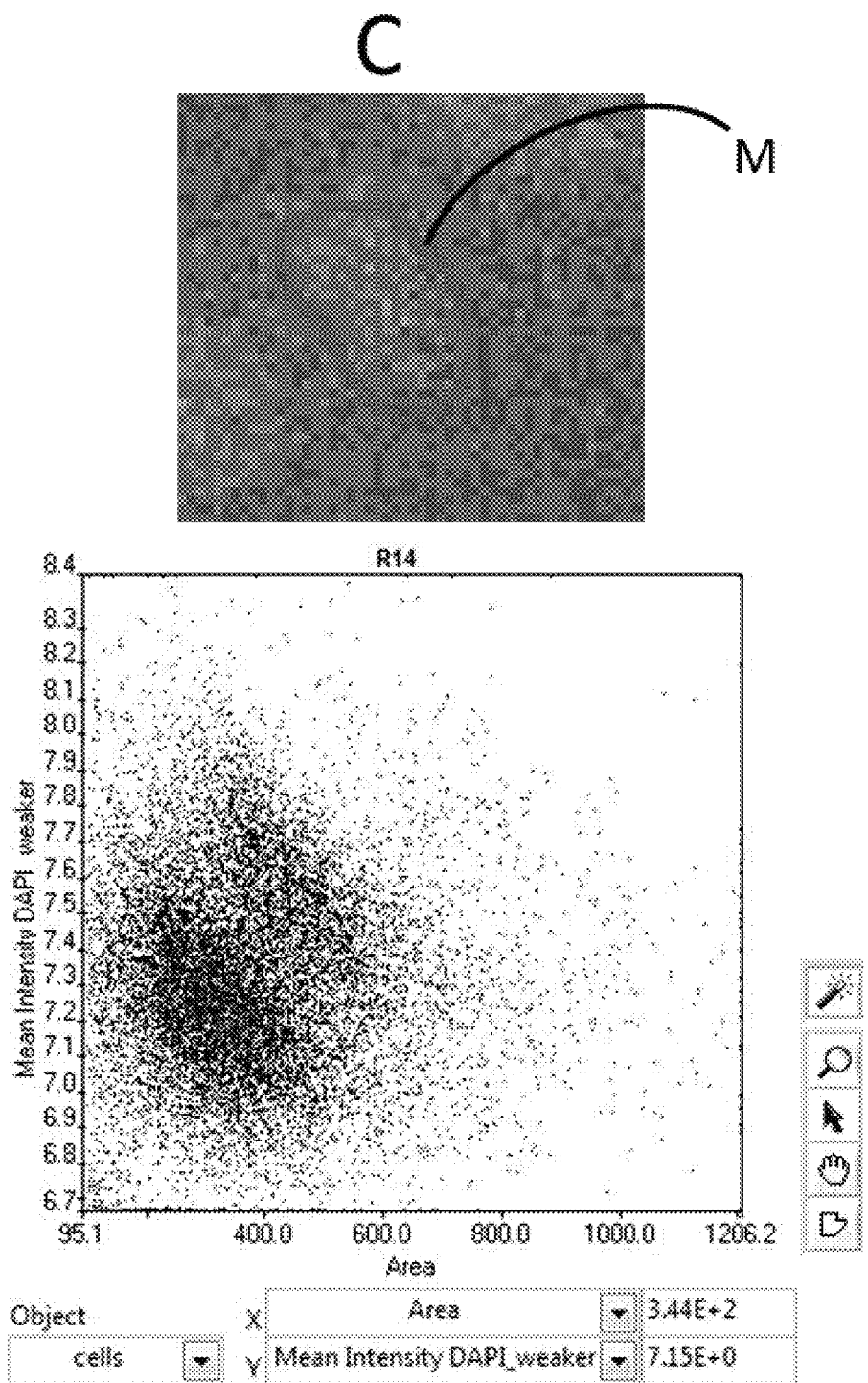

FIGS. 4A-4C illustrate recorded images of an individual fluorescence-stained cell nucleus in the upper part and the respective cytometric evaluation in the lower part of the image data of numerous cell nuclei.

The figures illustrate cytometric analyses based on images with transmission and segmentation as well as the analysis of fluorescence (with low signals) with G1 and G2 phases of the cell cycle. The images and evaluation for example A shown here occurred during an incremental movement of the cell samples with an illumination time of 100 ms. In the second example B, the cell samples are moved incrementally and are illuminated with an illumination time of 1 ms. A continuous movement of the cell samples occurred in example C, wherein the illumination time was 50 µs.

Examples A, B and C demonstrate conventional image recording with customary illumination parameters (A) as well as conventional image recording with an especially short illumination time (B) and image recording according to the present application with a short illumination time (C) with a continuously moving sample carrier. The content of information in the scatter charts (below), which is based directly upon the quantification of the fluorescence information, is comparable in all of the cases illustrated despite the significantly reduced load on the sample and the increased speed of data recording in case C according to the present application.

The essential properties of the analysis that is possible using the method according to the present application are illustrated in FIGS. 4A-4C on the basis of examples. The upper part of example A shows a section of a microscopic image that includes a single cell nucleus, recorded in the fluorescence mode by means of conventional microscopy, i.e. with incremental movement of the microscope table and illumination times in the range of 100 ms. In the associated lower section of the image for example A, the associated cytometric data analysis for numerous cell nuclei in a sample is represented by scatter charts.

The objective of the application is for two distinct clusters, which can be identified as sub-populations of the cell nuclei in mitotic phases G1 and G2, to be discernible in the scatter chart in which the average intensity of the detected fluorescence is represented over the surface. Under the conditions for example A, it would be technically possible to derive the position and contour data directly from the fluorescence image. Instead, a transmission image of the same location in the sample was chosen so that this information can be ascertained independently of the fluorescence image. The segmentation mask or respectively the object mask, of the cells shown is plotted in the upper image and designated M.

In the second example, example B, the same situation is portrayed as for example A but with a shorter illumination time of 1 ms. In this case, it is still possible in principle to determine the segmentation mask for the cells directly from the fluorescence image, but doing so is not robust for further analysis. According to the art, significantly shorter illumination times are unsuitable with regard to faster image recordings with an incremental movement of the microscope table, since the typical amount of time expended for the activation, acceleration and braking processes in the movement of the microscope table are relatively higher, and the forces and vibrations that occur during the recording of the images are harmful to living cells.

The situation according to the present application is illustrated in example C. As a result of the continuous movement of the microscope table, extremely short illumination times, for example 50 µs, are reasonable and permit high image recording rates while at the same time producing low forces and vibrations, which act upon the cells and the liquids.

Owing to the short illumination times, the harm to the cells caused by light is minimized. The use of the determined segmentation masks or object masks from the transmission mode makes it possible to perform a robust quantification of the fluorescence intensity of the cells despite a low signal-to-noise ratio of the fluorescence image. In the lower scatter chart, the representation of intensity data for numerous measured cell nuclei, which is relevant to the application, clearly indicates the same classification of sub-populations as in example B (according to the prior art).

While there has been shown and described what is considered to be preferred embodiments, it will, of course, be understood that various modifications and changes in form or detail could readily be made without departing from the spirit of invention. It is therefore intended that the invention be not limited to the exact forms described and illustrated, but should be constructed to cover all modifications that may fall within the scope of the appended claims.

LIST OF REFERENCE SIGNS

10 Arrangement
12 Light source
14 Condenser lens
16 Sample carrier
18 Table
22 Motor
24 Objective
26 Device
28 Digital camera 30 Optical element
32 Computer
34 Light source
36 Beam splitter

What is claimed is:

1. A method for a cytometric analysis of multiple cell samples by means of a microscope for examining multiple cell samples under a microscope, wherein the microscope is operated, alternatingly, in a fluorescence mode and in a transmission mode, and wherein at least one cell sample has at least one fluorescence marker, wherein the method comprises:
   continuously moving the cell samples in one plane relative to an optical system of the microscope having at least one microscope camera, wherein, during the movement of the cell samples, at least one or more images of a sub-region of the cell samples are recorded in the transmission mode at a time A and at least one or more images of the same sub-region of the cell samples are recorded in the fluorescence mode at a time B, the time A being earlier or later than the time B, by means of the at least one microscope camera, wherein a fluorescence quantification is carried out on the basis of the sub-region of the cell samples at the time B, and wherein the at least one or more images of the same sub-region of the cell samples in the transmission mode at the time A, and the at least one or more images of the same sub-region of the cell samples in the fluorescence mode at the time B are associated with each other, wherein the at least one or more images at the time A and the at least one or more images at the time B are modified based on a displacement path and displacement time of a sample carrier of the cell samples, so that the at least one or more images at the time A and the at least one or more images at the time B are assigned to the same sub-region of cell samples in transmission mode and fluorescence mode respectively, and one or more of the following;
   (a) wherein the positions and/or contours of cells or cell components of the cell samples are detected in the at least one or more images of the transmission mode at time A, and the detected intensities of the at least one or more images recorded in the fluorescence mode at time B are then analyzed as a function of the detected positions and/or contours of cells or cell components in the cell samples, and
   (b) wherein the positions and/or contours of cells or cell components of the cell samples are detected in the at least one or more images of the fluorescence mode at time B, and the detected intensities of the at least one or more images recorded in the transmission mode at time A are then analyzed as a function of the detected positions and/or contours of cells or cell components in the cell samples.

2. The method according to claim 1, wherein at least one image of a sub-region of the cell samples in the transmission mode that is offset in time, later or earlier, is modified with respect to a predetermined first image of the sub-region of the cell samples in the transmission mode as a function of a temporal offset or as a function of a relative displacement of the cell samples with respect to the at least one microscopy camera between the predetermined first image and a temporally offset image, so that the predetermined first image and the temporally offset image are associated with the same sub-region of the cell samples.

3. The method according to claim 1, wherein at least one image of a sub-region of the cell samples in the fluorescence mode that is offset in time, later or earlier, is modified with respect to a predetermined first image of the sub-region of the cell samples in the fluorescence mode as a function of a temporal offset or as a function of a relative displacement of the cell samples with respect to the at least one microscopy camera between the predetermined first image and a temporally offset image, so that the predetermined first image and the temporally offset image are associated with the same sub-region of the cell samples.

4. The method according to claim 1, wherein the movement of the cell samples is synchronized with a chronological sequence of the at least one or more images of the sub-region of the cell samples.

5. The method according to claim 1, wherein at least one image of the sub-region of the cell samples in the transmission mode is recorded in a first plane, and at least one image of the sub-region of the cell samples in the transmission mode is recorded in a second plane, which is different from the first plane.

6. The method according to claim 1, wherein at least two images of the sub-region of the cell samples are recorded in the fluorescence mode.

7. The method according to claim 1, wherein, after the at least one or more images of the sub-region of the cell samples have been recorded in the transmission mode at the time A, further images are recorded in the transmission mode or in the fluorescence mode for a sub-region of the cell samples that is adjacent to a preceding sub-region of the cell samples, wherein the further images are recorded in the same way for the adjacent sub-region as for the preceding subregion of the cell samples.

8. The method according to claim 1, wherein the images of the cell samples in the transmission mode for multiple sub-regions of the cell samples are all combined into one complete image in the transmission mode and the images of the cell samples in the fluorescence mode for multiple sub-regions of the cell samples are all combined into one complete image in the fluorescence mode.

9. The method according to claim 1, wherein the at least one or more images of the subregion of the cell samples recorded in the transmission mode at the time A and the at least one or more images of the same sub-region of the cell samples are recorded in the fluorescence mode at the time B are analyzed, or the images of the cell samples in the transmission mode for multiple sub-regions of the cell samples are all combined into one complete image in the transmission mode are analyzed, or the images of the cell samples in the fluorescence mode for multiple sub-regions of the cell samples are all combined into one complete image in the fluorescence mode are analyzed.

10. The method according to claim 9, wherein phase-contrast images are generated from the at least one or more images in the transmission mode at the time A or from the one complete image in the transmission mode.

11. The method of claim 1, wherein the microscope is operated in an epifluorescence mode.

12. The method of claim 1, wherein the cell samples are moved continuously and linearly.

13. The method of claim 1, wherein the at least one or more images of the same sub-region of the cell samples are recorded at least in sections.

14. The method of claim 1, wherein the one or more images are digitized.

15. The method of claim 1, wherein the at least one or more images of the same sub-region of the cell samples in the fluorescence mode at the time B are associated with each other locally.

16. The method of claim 5, wherein the second plane is a defocused plane.

17. The method of claim 6, wherein the at least two images of the sub-region of the cell samples are recorded in an epifluorescence mode.

18. The method of claim 7, wherein the at least one or more images are recorded in the transmission mode or in the fluorescence mode for a sub-region of the cell samples that is immediately adjacent to the preceding sub-region of the cell samples.

19. The method of claim 9, wherein the images are automatically analyzed.

* * * * *